(12) United States Patent
Cohen et al.

(10) Patent No.: US 6,414,019 B1
(45) Date of Patent: Jul. 2, 2002

(54) SYNERGISTIC MIXTURES OF SELECTED AMINO ACIDS

(75) Inventors: Yigal Cohen, Kiryat Ono; Moshe Korat, Meitar; Dan Zvi-Tov, Omer, all of (IL)

(73) Assignee: Agrogene Ltd., Kiryat Ono (IL)

( * ) Notice: Subject to any disclaimer, the term of this patent is extended or adjusted under 35 U.S.C. 154(b) by 0 days.

(21) Appl. No.: 09/402,825

(22) PCT Filed: Apr. 8, 1998

(86) PCT No.: PCT/IL98/00167

§ 371 (c)(1),
(2), (4) Date: Oct. 12, 1999

(87) PCT Pub. No.: WO98/46078

PCT Pub. Date: Oct. 22, 1998

(30) Foreign Application Priority Data

Apr. 16, 1997 (IL) .................................................. 120677
Feb. 17, 1998 (IL) .................................................. 123346

(51) Int. Cl.$^7$ ........................ A01N 47/10; A01N 37/12; A01N 37/44
(52) U.S. Cl. ........................ 514/491; 514/476; 514/561
(58) Field of Search ................................ 514/476, 491, 514/561

(56) References Cited

FOREIGN PATENT DOCUMENTS

| WO | 9515684 | 6/1995 |
| WO | 9622690 | 8/1996 |

OTHER PUBLICATIONS

Tomlin, The Pesticide Manual Incorporating The Agrochemicals Handbook, 10$^{th}$Ed. (1995) pp. 635&636.*
Ryals et al., "Sytemic Acquired Resistance", *The Plant Cell*, vol. 8, pp. 1809–1819, (1996).
GISI et al., "Synergistic interaction of Fungicides in Mixtures", Phytopathology, vol. 86, No. 11, pp. 1273–1279, (1996).
Cohen et al., "B–Aminobutyruc Acid Induces the Accumulation of Pathogenesis–Related Proteins in Tomato (Lycopersicon esculenttum L.) Plant and Resistance to Late Blight Infection Caused by Phytophthora infestans", *Plant Physiol*, vol. 104, pp. 59–66, (1994).

* cited by examiner

*Primary Examiner*—Allen J. Robinson
(74) *Attorney, Agent, or Firm*—Browdy and Neimark

(57) ABSTRACT

Novel synergistic fungicidal compositions used for protecting seeds, plants and other vegetative material against fungi contain a mixture of one or more compounds selected from group A and one or more compounds selected from group B. Compounds from group A are selected from Beta-Amino butyric acid and its N-benzoyl-octyl ester derivatives. Compounds from group B are selected from the group of fosetyl aluminum, dimethomorph, a mixture of folpet and ofurace (45:5), folpet fencaramid (Bayer SZX), mancozeb, cymoxynil, methalaxyl, the single optical isomer of metalaxyl, a mixture of cymoxamil and mancozeb (4:1), copper sulfate, copper hydroxide, copper sulfate hydrate, azoxystrobin, and acidenzolar-s-methyl.

11 Claims, No Drawings

SYNERGISTIC MIXTURES OF SELECTED AMINO ACIDS

This application is a 371 of PCT/IL 98,00167, filed Apr. 8, 1998.

The present invention concerns synergistic fungicidal mixtures. The present invention more particularly concerns synergistic mixture of β-aminobutyric acid (hereinafter. referred to as BABA) and its N-benzoyl-octyl ester derivatives for the control of plant diseases.

BACKGROUND OF THE INVENTION

Fungicides are often combined in mixtures for 3 main reasons: 1 to widen the spectrum of antifungal activity to control several diseases occurring simultaneously in a crop 2. to exploit synergistic interaction between fungicides, by which the overall activity is increased and the concentration of the compounds reduced, and 3. to delay the selection process of resistant fungal individuals to one component of the mixture (Gisi, Phytopathology 86 1273–1279,1996).

Avoidence of plant disease in agricultural production may be accomplished not only by using fungicides or fungicidal mixtures but also by using "plant activators", molecules which enhance the natural resistance (defense) of the plant. Such activators which have no direct fungicidal effect on the pathogen (Ryals et al The Plant Cell 8: 1809–1819,1996), induce systemic acquired resistance (SAR) in the plant several days after application (Ibid).

To date only few molecules were reported to induce SAR in crop plants viz. salicylic acid (SA), 2,6-dichloroisonicotinic acid (INA) benzol (1,2,3) thiadiazole -7-carbothiouic acid S-methyl ester (BTH) (Ibid), and DL-3-amino butyric acid (BABA, Cohen et al Plant Physiology 104: 56–59,1994).

However whereas SA, INA or BTH have to be applied to the crop ahead of infestation (Ryals, et al Ibid) BABA can be applied post-infectionaly (Cohen et al Ibid).

The idea behind the present invention is to combine two methods of disease control—the direct-kill method operating on the target pathogen and the indirect method of activating the natural defense approach of the crop plant. Such two methods are combined by using mixtures of a fungicide or fungicides (direct-kill) with BABA or its N-benzoyl-octyl ester derivative(SAR).

We show here that such mixtures are synergistic in controlling plant diseases.

OBJECTIVES OF THE INVENTION

It is the objective of the present invention to provide novel mixtures of fungicides of β-aminobutyric acids. It is an objective of the present invention to provide a synergistic mixture of BABA and/or its N-benzoyl-, octyl ester derivative with various other fungicides.

SUMMARY OF THE INVENTION

In accordance with the present invention there is provided synergistic fungicidal compositions comprising one or more compounds selected from Group A and one or more compounds selected from Group B; wherein the compounds of Group A are selected from the group consisting of DL-3 aminobutyric acid and its N-Benzoyl octyl ester, and the compounds of Group B are selected from the group consisting of fosetyl aluminum, dimethomorph, a mixture of folpet and ofurace (45:5), folpet, fencaramid (Bayer SZX), mancozeb, cymoxanil, methalaxyl, the single optical isomer of metalaxyl, a mixture of cymoxamil and mancozeb (4:1), copper sulfate, copper hydroxide, copper sulfate hydrate, azoxystrobin, and acibenzolar-s-methyl.

The present invention also provides an improved method of controlling fungi, especially late blight and downy mildews, applying to the plant a composition containing an effective amount of one of these mixtures. The present invention further provides an improved method of controlling $Phytophthora\ infertan$ in potato or tomatoe, $Pseudoperonospora\ cubensis$ in cucumber or melon, $Plasmopera\ viticola$ in grapes, and $Peronospora\ tabacina$ in tabacco.

DETAILED DESCRIPTION OF THE INVENTION

Methodology

Plants 1. Potato (cultivar Alpha) were grown from tubers in 1 liter pots in sandy soil in the greenhouse. At 5 weeks after planting when they had several shoots in a pot, with 10–12 leaves per shoot, plants were taken for assays.

2. Cucumber (cultivate Dlila ) plants were grown from seed in 0.251 liter pots containing sandy soil in the greenhouse. At 3 weeks after sowing, when they developed 2 leaves they were used.

3. Grapes (cultivate Superior) plants were grown from cuttings (first in perlite and then in sandy soil) in pots in the greenhouse. At 8 weeks after planting leaves were detached for experiments.

Fungal Pathogens. Potatoes were inoculated with sporangic of $Phytophthora\ infestans$ (resistant to metalaxyl). Cucumbers were inoculated with sporangia of $Pseudoperonospora\ cubensis$ (resistance to metalaxyl). Grapes were inoculated with $Plasmopara\ viticola$ Chemicals.

1. DLβ-amino-butanoic acid (BABA)
2. DL-4-benzoyl-3-amino butanoic acid octylester (039–81)
3. Cymoxanil (Curzate)
4. phosetyl-aluminium (Alliette)
5. Mancozeb
6. Folpet
7. Metalaxyl, metalaxyl-Gold
8. Copper sulphate, copper hydroxide
9. (Mancozeb+dimethomorph, prepacked 600 g+90 g a.i.per 1 kg)
10. (Mancozeb+metalaxyl, prepacked 560 g+75 g a.i. per 1 kg)
11. Folpet+ofurace, 450 g+60 g a.i. per 1 kg)
12. Bayer-SZX (Fencaramid)
13. Mancozeb+Cymoxanil (4:1)
14. Azoxystrobin
15. Acibenzolar-s-methyl
16. Dimethomorph Except BABA which was dissolved in water, all other chemicals or prepacked mixtures produced a suspension or emulsion in water.

Spraying The chemicals were sprayed onto the upper leaf surfaces of either potatoes or cucumbers with the aid of a fine glass atomizer. Control plants were sprayed with water. Experiments with grapes were carried out using 12 mm leaf discs floating on 1 ml of the test compound(s) in 24—well titer plates, upperside down.

Inoculation

Potatoes and cucumbers were inoculated one day after spraying. Grape leaf discs were inoculated soon after floating.

Inoculation of potato was done by spraying the upper leaf surfaces of the plants with a sporangial suspension containing 2000 sporangia/ml. Sporangia were harvested 0.5 h before inoculation from infected potato tuber slices. Cucumbers were sprayed with a sporangial suspension containing 1500 sporangia/ml. Sporangia were harvested from infected cucumber plants kept in humid growth chambers (at 15° C.). Leaf discs of grapes were inoculated with 2 sporangial droplets containing each 300 sporangia. Sporangia were harvested from infected leaves kept in petri dishes on wet filter paper at 15° C. Inoculated plants or titer plates were placed in a dew chamber at 18° C. overnight and then transferred to a growth chamber at 20° C. (12 h light/day 100 pE.m$^{-2}$.S$^{-1}$) for symptom production (late blight in potato and downy mildew in cucumber), or for sporulation of *P. viticola* in grape leaf discs.

General Procedure for Tabacco

One month old tobacco plants (cv.xanthi nc.). were sprayed onto their foliage with the test compounds. Two days later they were inoculated with $10^4$ spores/ml of *Perouospora latacin* of either the S or the R strain. Inoculated plants were placed in 100% relative humidity over night and then incubated at 20° C. with 12 h light/day. A week after innoculation plants were again placed at 100%-RH at 18° C. in the dark to induce fungal sporulation. Sporulation was quantitated by removing 2 cm$^2$ leaf discs from each leaf and counting with the aid of a haemocytometer. The extent of sporulation inhibition was calculated relative to that in control (untreated) inoculated plants. $Ed_{go}$ was computed after linear regression and of was calculated according to Wadely.

General Procedure for Grapes

Leaf discs (2-cm$^2$) were removed from the top leaves of grape plants (cv. Superior) grown in the greenhouse. Discs were floated (lower surface uppermost on the test solutions over filter paper of 9 cm diameter). Petri dishes. Leaf discs were immediately innoculated with 2 (10 ml) droplets of sporangial suspension ($10^4$/ml) of *Plasmopara viticola* per disc. Dishes were inculoated at 20° C. with 12 h light/day for 10 days until fungal sporulation was quantified.

Disease Assessment

At the time intervals post inoculation specified in the Examples, infected leaf area in potato and cucumber was assessed visually. In control inoculated plants most or all of the foliage (80–100%) was devastated by the disease. Percentage control of the disease by a chemical treatment was calculated as % control=(1−x/y)×100 whereas x=proportion leaf area diseased in treated plants and y=proportion leaf area diseased in control plants.

In grapes, proportion of leaf discs showing sporulation were similarly used.

Calculation of Control Efficacy and Synergism

Each chemical and each mixture was applied to plants at various doses of the active ingredient. Dose—response curves were produced and transferred to log—dose probit response curves as described by Kosman and Cohen (Phytopatholagy 86: 1263–1272, 1996). ED$_{90}$ values (dose required for achieving 90% control of the disease) taken from the log-probit 7 curves were used to calculate the Cotoxicity Factor (CF) according to the Wadely procedure (Kosman and Cohen, Ibid; Gisi phytopatcology 86: 1273–1279,1966). "CF" is defined as the ratio between the expected dose and the observed dose that provide the same level of disease control (Kosman and Cohen, Ibid). The observed dose of each component of a mixture is taken from the experiment and the expected dose of all mixture made of that components is calculated by the Wadely formula:

$$ED_{90} \text{ expected} = \frac{a+b}{\frac{a}{ED_{90} \text{ obs.A}} + \frac{b}{ED_{90} \text{ obs.B}}}$$

where a and b are the absolute amounts of the components A and B in a mixture and ED$_{90}$. obs.A and Ed$_{90}$ obs.B are the Ed$_{90}$ values of A and B obtained by the experiment. CF values of>2.0 are considered to represent a strongly synergistic mixture (Gisi, Ibid).

According to a further feature of the invention, there is provided a fungicidal composition which comprises a compound of the invention together with carrier. The active compound can be employed as a wide variety of formulations, for example as an aqueous dispersion, a dispersible powder, as seed dressing, granules or dust. As a dispersion the composition comprises an active compound together with a dispersing agent dispersed in a liquid medium, preferably water. It can be in a form of a concentrated primary composition which requires dilution with a suitable quantity of water or other diluent before application. Such primary compositions are a convenient way of supplying the consumer and preferred example is a dispersible powder. A dispersible, powder comprises an active compound, a dispersing agent and solid carrier. The latter can be, for example, kaolin, talc, or diatomaceous earth and in addition, the dispersible powder can contain a wetting agent.

Other formulations include seed dressing, granules or dusts, in all of which the active compound is associated with a solid carrier and which are intended for direct application. They can be made by methods well known in the art. Preferably all compositions comprising a solid carrier are made by mixing the active compound in particulate form with a particulate carrier.

The concentration of the active compound in the composition of the invention can vary widely. In the case of a primary composition it is preferably from 15% to 95% by weight, more especially from 50% to 80% by weight. A composition intended for direct application to a crop preferably comprises from 0.001% to 10% more, especially from 0.005% to 5% by weight of the active compound, although the aerial spraying of a crop is contemplated compositions having higher concentrations, for example up to 30% by weight may be chosen in preference.

The fungicidal composition of the present invention may be applied as a ready-mixed composition, as a tank mix, or applying the compounds of each group separately.

Following the methods outlined above numerous mixtures were prepared and their activity against a variety of diseases were studied. The results of 35 studies are listed in Tables 1–35.

While the invention will now be described in connection with certain preferred embodiments in the following examples it will be understood that it is not intended to limit the invention to these particular embodiments. On the contrary, it is intended to cover all alternatives, modifications and equivalents as be included within the scope of the invention, as defined by the appended claims. Thus, the following examples which include preferred embodiments, will serve to illustrate the practice of this invention, it being understood that the particulars shown are by way of example and for purposes of illustrative discussion of preferred embodiments of the present invention only and are presented in the cause of providing what is believed to be the most useful and readily understood description of procedures as well as of the principles and conceptual aspects of the invention.

TABLE 1

CONTROL OF LATE BLIGHT IN POTATO BY BABA COPPER SULFATE HYDRATE MIXTURE[a]

| Compounds | Ratio | \multicolumn{6}{c}{Percent Disease Control[b] mg/L Active Ingredient} | $ED_{90}$ mg/L | CF |
|---|---|---|---|---|---|---|---|---|---|
| | | 2 | 8 | 32 | 125 | 250 | 1000 | | |
| BABA | — | — | — | 0 | 0 | 0 | 13 | 2678 | — |
| $Cu^{+2}$ | — | 0 | 0 | 63 | 83 | — | — | 143 | — |
| BABA + $Cu^{+2}$ | 80 + 20 | 0 | 0 | 13 | 88 | — | — | 126 | 4.7 |
| | 70 + 30 | 0 | 0 | 50 | 93 | — | — | 101 | 4.2 |
| | 60 + 40 | 0 | 0 | 85 | 93 | — | — | 85 | 3.9 |

[a] 5 days post inoculation
[b] Control plants showed 100% leaf blight

TABLE 2

CONTROL OF LATE BLIGHT IN POTATO BY BABA CYMOXANIL MIXTURE (CURZATE ®)[a]

| Compounds | Ratio | \multicolumn{5}{c}{Percent Disease Control[b] mg/L Active Ingredient} | $ED_{90}$ mg/L | CF |
|---|---|---|---|---|---|---|---|---|
| | | 4 | 16 | 62 | 250 | 1000 | | |
| BABA | — | | 3 | 24 | 18 | 64 | 1498 | — |
| Cymoxanil | — | 36 | 73 | 64 | 98 | | 128 | — |
| BABA + Cymoxanil | 80 + 20 | 9 | 9 | 3 | 79 | — | 294 | 1.6 |
| | 50 + 50 | 73 | 76 | 82 | 98 | — | 114 | 2.1 |

[a] 5 days post inoculation
[b] Control plants showed 83% leaf blight

TABLE 3

CONTROL OF LATE BLIGHT IN POTATO BY BABA FOSETYL ALUMINUM MIXTURE[a]

| Compounds | Ratio | \multicolumn{4}{c}{Percent Disease Control[b] mg/L Active Ingredient} | $ED_{90}$ mg/L | CF |
|---|---|---|---|---|---|---|---|
| | | 16 | 62 | 250 | 1000 | | |
| \multicolumn{8}{c}{Cultivar Cara[b]} |
| BABA | | 9 | 9 | 9 | 24 | 3233 | — |
| Fosetyl – Al | | 9 | 24 | 24 | 70 | 1390 | — |
| BABA + | 75 + 25 | 9 | 9 | 39 | 70 | 1311 | 1.9 |
| Fosetyl – Al | 25 + 75 | 9 | 9 | 39 | 79 | 1142 | 1.4 |
| \multicolumn{8}{c}{Cultivar Draga[c]} |
| BABA | | 0 | 0 | 0 | 53 | 1533 | — |
| Fosetyl – Al | | 33 | 33 | 50 | 93 | 856 | — |
| BABA + | 75 + 25 | 67 | 67 | 93 | 93 | 639 | 1.7 |
| Fosetyl – Al | 25 + 75 | 0 | 0 | 93 | 100 | 245 | 3.9 |

[a] 5 days post inoculation
[b] Contact plants showed 83% leaf blight
[c] Contact plants showed 38% leaf blight

TABLE 4

CONTROL OF LATE BLIGHT IN POTATO BY BABA MIXTURES OF MANCOZEB + DIMETHOMORPH MIXTURES[a]

| Compounds | Ratio | \multicolumn{5}{c}{Percent Disease Control[b] mg/L Active Ingredient} | $ED_{90}$ mg/L | CF |
|---|---|---|---|---|---|---|---|---|
| | | 4 | 16 | 62 | 250 | 1000 | | |
| BABA | — | — | 3 | 24 | 18 | 64 | 1498 | — |
| MANCOZEB + DIMETHOMORPH | — | 70 | 73 | 82 | 98 | — | 115 | — |
| BABA + (MANCOZEB[c] + DIMETHOMORPH) | 80 + 20 | 64 | 73 | 70 | 82 | — | 287 | 1.5 |
| | 50 + 50 | 85 | 70 | 70 | 91 | — | 189 | 1.1 |

[a] 5 day post innoculation
[b] Control Plants showed 83% leaf blight
[c] 60% Mancozeb & 9% Dimethomorph

TABLE 5

CONTROL OF LATE BLIGHT IN POTATO BY BABA FOLPET/OFURACE (45 + 5) MIXTURE[a]

| Compounds | Ratio | Percent Disease Control[b] @ mg/L Active Ingredient | | | | | $ED_{90}$ mg/L | CF |
|---|---|---|---|---|---|---|---|---|
| | | 4 | 16 | 62 | 250 | 1000 | | |
| BABA | | — | 14 | 14 | 14 | 36 | 2617 | |
| FOLPET/ OFURACE | | 77 | 89 | 99 | 100 | — | 19 | |
| BABA + (FOLPET/ OFURCE) | 50 + 50 | 74 | 81 | 99 | 100 | — | 22 | 1.8 |

[a]7 days
[b]Control plants showed 88% leaf blight

TABLE 6

CONTROL OF LATE BLIGHT IN POTATO BY BABA FOLPET - CYMOXANIL MIXTURE[a]

| Compounds | Ratio | Percent Disease Control[b] mg/L Active Ingredient | | | | $ED_{90}$ mg/L | CF |
|---|---|---|---|---|---|---|---|
| | | 16 | 62 | 250 | 1000 | | |
| BABA | | 22 | 22 | 22 | 69 | 1481 | |
| FOLPET | | 81 | 95 | 98 | 100 | 84 | |
| CYMOXANIL | | 83 | 86 | 91 | 100 | 183 | |
| BABA + FOLPET + CYMOXANIL | 60 + 25 + 15 | 72 | 89 | 98 | 100 | 95 | 2.5 |
| | 25 + 60 + 15 | 92 | 86 | 95 | 100 | 104 | 1.3 |

[a]6 day post innoculation
[b]Control plants showed 80% leaf blight

TABLE 7

CONTROL OF LATE BLIGHT IN POTATO BY THE N - BENZOYL OCTYL ESTER OF BABA AND FENCARAMID[a]

| Compounds | Ratio | Percent Disease Control mg/L Active Ingredient[b] | | | | | | | $ED_{90}$ mg/L | CF |
|---|---|---|---|---|---|---|---|---|---|---|
| | | 2 | 8 | 32 | 125 | 250 | 1000 | 2000 | | |
| BABA Derivative | | — | — | — | 15 | 25 | 50 | 53 | 2395 | |
| Fencaramid | | 0 | 50 | 98 | 100 | — | — | — | 19 | |
| BABA DERIVATIVE + FENCARAMID | 80 + 20 | 44 | 63 | 85 | 100 | — | — | — | 31 | 3.0 |
| | 90 + 10 | 13 | 50 | 56 | 94 | — | — | — | 97 | 1.8 |

[a]4 day post innoculation
[b]Control plants at 100% leaf blight

TABLE 8

CONTROL OF LATE BLIGHT IN POTATO BY N-BENZOYL OCTYL ESTER OF BABA, Cu (OH)$_2$, (as 50% a.i), MANCOZEB[a]

| Compounds | Ratio | Percent Disease Control b mg/L Active Ingredient | | | | | $ED_{90}$ mg/L | CF |
|---|---|---|---|---|---|---|---|---|
| | | 4 | 16 | 62 | 250 | 1000 | | |
| N-benzoyl octyl ester derivative of BABA | | — | 3 | 25 | 25 | 75 | 1261 | |
| Cu(OH)$_2$ | | 0 | 0 | 13 | 75 | — | 298 | |

TABLE 8-continued

CONTROL OF LATE BLIGHT IN POTATO BY N-BENZOYL OCTYL ESTER OF BABA, Cu (OH)$_2$, (as 50% a.i), MANCOZEB[a]

| Compounds | Ratio | Percent Disease Control [b] mg/L Active Ingredient | | | | | ED$_{90}$ mg/L | CF |
|---|---|---|---|---|---|---|---|---|
| | | 4 | 16 | 62 | 250 | 1000 | | |
| Cu(OH)$_2$ + Mancozeb | 70 + 30 | 0 | 3 | 44 | 50 | — | 416 | |
| N-benzoyl octyl ester derivative of BABA + Cu(OH)$_2$ | 80 + 20 | 3 | 3 | 25 | 75 | | 300 | 2.6 |
| N-benzoyl octyl ester derivative of BABA + Cu(OH)$_2$ + mancozeb | 80 + 14 + 6 | 3 | 3 | 75 | 83 | | 239 | 3.8 |

[a] 7 days post innoculation
[b] Control plants showed 100% leaf blight

TABLE 9

CONTROL OF LATE BLIGHT IN POTATO BY N-BENZOYL OCTYL ESTER DERIVATIVE OF FOLPET/OFURACE (45 + 5) AND THEIR MIXTURES[a]

| Compounds | Ratio | Percent Disease Control @ mg/L Active Ingredient[b] | | | | | ED$_{90}$ mg/L | CF |
|---|---|---|---|---|---|---|---|---|
| | | 4 | 16 | 62 | 250 | 1000 | | |
| N-benzoyl octyl ester derivative of BABA | | — | 0 | 0 | 0 | 25 | 2011 | |
| Folpet + Ofurace (9 + 1) | | 0 | 0 | 3 | 73 | — | 301 | |
| N-benzoyl ester derivative of BABA + (Folpet Ofurace | 67 + 33 | 0 | 13 | 75 | 100 | — | 74 | 9.5 |
| | 50 + 50 | 8 | 8 | 69 | 100 | — | 82 | 6.4 |
| | 33 + 67 | 3 | 19 | 75 | 98 | — | 15 | 3.6 |

[a] 7 days post innoculation
[b] Control plants showed 100% leaf blight

TABLE 10

CONTROL OF LATE BLIGHT IN POTATO BY N-BENZOYL OCTYL ESTER DERIVATIVE OF BABA, AND MANCOZEB + CYMOXANIL; 4:1 AND THEIR MIXTURES[a]

| Compounds | Ratio | Percent Disease Control[b] mg/L Active Ingredient | | | | | ED$_{90}$ mg/L | CF |
|---|---|---|---|---|---|---|---|---|
| | | 4 | 16 | 62 | 250 | 1000 | | |
| N-benzoyl octyl ester derivative of BABA | — | 0 | 0 | 0 | 0 | 25 | 2011 | |
| Mancozeb + Cymoxanil | — | 0 | 25 | 25 | 75 | — | 313 | |
| N-benzoyl octyl ester derivative of BABA + Mancozeb + Cymoxanil | 67:33 | 25 | 68 | 70 | 95 | — | 169 | 4.3 |
| | 50:50 | 5 | 63 | 88 | 98 | — | 95 | 5.7 |
| | 33:67 | 25 | 69 | 90 | 100 | — | 52 | 8.3 |

[a] 7 days Post innoculation
[b] Control plant showed 100% leaf blight

TABLE 11

CONTROL OF LATE BLIGHT IN POTATO BY N-BENZOYL OCTYL ESTER
DERIVATIVE OF BABA, FOLPET AND THEIR MIXTURES[a]
Percent Disease Control[b]
mg/L Active Ingredient

| Compounds | Ratio | 4 | 16 | 62 | 250 | 500 | 1000 | 2000 | $ED_{90}$ mg/L | CF |
|---|---|---|---|---|---|---|---|---|---|---|
| N-benzoyl octyl ester derivative of BABA | | — | — | — | 63 | 69 | 85 | 89 | 1514 | |
| Folpet | | 70 | 75 | 90 | 95 | — | — | — | 141 | |
| N-benzoyl octyl ester derivative of BABA + Folpet | 80 + 20 | 50 | 80 | 85 | 93 | — | — | — | 167 | 3.1 |
| | 67 + 33 | 13 | 76 | 86 | 96 | — | — | — | 130 | 2.8 |
| | 33 + 67 | 63 | 76 | 78 | 88 | — | — | — | 224 | 0.9 |
| | 20 + 80 | 25 | 75 | 73 | 97 | — | — | — | 140 | 1.2 |

[a]4 days post innoculation
[b]Control plants showed 100% leaf blight

TABLE 12

CONTROL OF LATE BLIGHT IN POTATO BY N-BENZOYL OCTYL ESTER
DERIVATIVE OF BABA, FENCARAMID (BAYER SZX) AND THEIR MIXTURES[a]
Percent Disease Control[b]
mg/L Active Ingredient

| Compounds | Ratio | 2 | 8 | 31 | 25 | 500 | 1000 | 2000 | $ED_{90}$ mg/L | CF |
|---|---|---|---|---|---|---|---|---|---|---|
| N-benzoyl octyl ester derivative of BABA | | — | — | — | 15 | 25 | 50 | 53 | 3204 | — |
| Fencaramid | | 0 | 50 | 98 | 100 | — | — | — | 19 | — |
| N-benzoyl octyl ester derivative of BABA + Fencarmid | 90:10 | 13 | 50 | 56 | 94 | — | — | — | 83 | 2.2 |
| | 80:20 | 44 | 63 | 85 | 100 | — | — | — | 31 | 3.0 |

[a]5 days post innoculation
[b]Control plants showed 100% leaf blight

TABLE 13

CONTROL OF DOWNY MILDEW IN CUCUMBER BY BABA,
COPPER SULPHATE HYDRATE (EXPRESSED AS mg/L
$Cu^{++}$) AND THEIR MIXTURES[a]

| Compounds | Ratio | 16 | 62 | 250 | 1000 | $ED_{90}$ mg/L | CF |
|---|---|---|---|---|---|---|---|
| BABA | | 43 | 43 | 57 | 72 | 1468 | |
| | Ratio | 2 | 8 | 32 | 125 | | |
| $Cu^{++}$ | | 57 | 72 | 80 | 89 | 105 | |
| BABA + $Cu^{++}$ | 80 + 20 | 72 | 72 | 86 | 89 | 102 | 4.0 |
| | 70 + 30 | 57 | 72 | 72 | 89 | 111 | 2.7 |
| | 60 + 40 | 57 | 72 | 86 | 89 | 102 | 1.9 |

[a]7 days post innoculation
[b]Control plants showed 88% leaf infection

TABLE 14

CONTROL OF DOWNY MILDEW IN CUCUMBER BY BABA, (EXPRESSED AS $Cu(OH)_2$)
($Cu(OH)_2$ + MANCOZEB) AND THEIR MIXTURES

| Compounds | Ratio | 4 | 16 | 62 | 250 | 1000 | $ED_{90}$ mg/L | CF |
|---|---|---|---|---|---|---|---|---|
| BABA | | — | 33 | 33 | 50 | 67 | 1576 | |
| $Cu(OH)_2$ | | 67 | 67 | 77 | 80 | — | 304 | |
| $Cu(OH)_2$ + mancozeb | 70 + 30 | 67 | 67 | 83 | 93 | — | 174 | |
| BABA + $Cu(OH)_2$ | 80 + 20 | 67 | 70 | 77 | 90 | — | 210 | 4.1 |
| BABA + $Cu(OH)_2$ + mancozeb | 80 + 14 + 6 | 70 | 70 | 90 | 90 | — | 191 | 3.2 |

[a]4 days post innoculation
[b]Control plants were 83% infected

TABLE 15

CONTROL OF DOWNY MILDEW IN CUCUMBER BY BABA, (FOLPET/OFURACE 45 + 5)

| Compounds | Ratio | \multicolumn{5}{c}{Percent Disease Control[b] mg/L Active Ingredient} | $ED_{90}$ mg/L | CF |
|---|---|---|---|---|---|---|---|---|
|  |  | 4 | 16 | 62 | 250 | 1000 |  |  |
| BABA | — | 0 | 29 | 57 | 71 | — | 1273 | — |
| Vamin |  | 43 | 57 | 71 | 91 | — | 206 | — |
| BABA + Vamin | 67 + 33 | 14 | 21 | 57 | 97 | — | 166 | 2.8 |
|  | 50 + 50 | 14 | 43 | 71 | 89 | — | 217 | 2.1 |
|  | 33 + 67 | 29 | 57 | 74 | 89 | — | 214 | 1.3 |

[a] 7 days post innoculation  
[b] Control plants were 88% infected

TABLE 16

CONTROL OF DOWNY MILDEW CUCUMBER BY BABA AND (MANCOZEB + CYMOXANIL; 4:1)

| Compounds | Ratio | 4 | 16 | 62 | 250 | 1000 | $ED_{90}$ mg/L | CF |
|---|---|---|---|---|---|---|---|---|
| BABA | — | 0 | 29 | 57 | 71 | — | 1273 | — |
| (Mancozeb + Cymoxanil) |  | 14 | 80 | 97 | 100 | — | 33 | — |
| BABA + (Mancozeb + Cymoxanil) | 67 + 33 | 21 | 57 | 77 | 97 | — | 135 | 0.7 |
|  | 50 + :50 | 57 | 74 | 100 | 100 | — | 20 | 3.2 |
|  | 33 + :67 | 29 | 94 | 100 | 100 | — | 14 | 3.5 |

[a] 7 days post innoculation  
[b] Control plants were 88% infected

TABLE 17

CONTROL OF DOWNY MILDEW CUCUMBER BY BABA AND (MANCOZEB + METALAXYL)

| Compounds | Ratio | 4 | 16 | 62 | 250 | 1000 | $ED_{90}$ mg/L | CF |
|---|---|---|---|---|---|---|---|---|
| BABA | — | 0 | 15 | 3 | 59 | — | 1443 | — |
| Mancozeb + Metalaxyl |  | 34 | 53 | 71 | 82 | — | 268 | — |
| BABA + Mancozeb + Metalaxyl | 88 + 12 | 0 | 0 | 9 | 96 | — | 221 | 4.3 |
|  | 75 + 25 | 18 | 44 | 53 | 81 | — | 281 | 2.4 |
|  | 50 + 50 | 38 | 76 | 76 | 96 | — | 150 | 3.0 |

[a] 6 days post innoculation  
[b] Control plants were 88% infected

TABLE 18

CONTROL OF DOWNY MILDEW IN CUCUMBER BY BABA, FOLPET & METALAXYL[a] (87:13)

| Compounds | Ratio | 4 | 16 | 62 | 250 | 1000 | $ED_{90}$ mg/L | CF |
|---|---|---|---|---|---|---|---|---|
| BABA | — | 0 | 15 | 3 | 59 | — | 1443 | — |
| Folpet & Metalaxy (87 + 13) |  | 0 | 0 | 56 | 76 | — | 280 | — |
| BABA + [Folpet + metalaxyl] | 88 + 12 | 12 | 0 | 59 | 81 | — | 260 | 3.7 |
|  | 75 + 25 | 68 | 53 | 56 | 71 | — | 393 | 1.8 |
|  | 50 + 50 | 0 | 38 | 62 | 68 | — | 339 | 1.4 |

[a] 6 days post innoculation  
[b] Control plants were 88% infected

TABLE 19

CONTROL OF DOWNY MILDEW IN CUCUMBER BY BABA, FOLPET & METALAXYL[a], (7 + 1) (MANCOZEB + METALAXYL), (FOLPET + OFURACE) AND THEIR MIXTURES

| Compounds | Ratio | 4 | 16 | 62 | 250 | 1000 | $ED_{90}$ mg/L | CF |
|---|---|---|---|---|---|---|---|---|
| BABA | — | 12 | 19 | 25 | 31 | — | 3218 | — |
| Folpet + metalaxyl |  | 62 | 82 | 90 | 97 | — | 112 | — |
| BABA + [Folpet + metalaxyl] | 80:20 | 62 | 70 | 80 | 85 | — | 247 | 2.0 |
|  | 50:50 | 75 | 77 | 80 | 97 | — | 133 | 1.6 |
| (Mancozeb + metalaxyl) |  | 77 | 85 | 95 | 97 | — | 100 | — |
| BABA (Mancozeb + metalaxyl | 80 + 20 | 82 | 87 | 92 | 97 | — | 105 | 4.2 |
|  | 50 + 50 | 82 | 92 | 97 | 97 | — | 92 | 2.1 |
| (Folpet + Ofurace) |  | 37 | 50 | 62 | 82 | — | 279 | — |
| BABA + (Folpet + Ofurace) | 80:20 | 50 | 62 | 80 | 92 | — | 187 | 5.5 |
|  | 50:50 | 77 | 97 | 92 | 100 | — | 33 | 15.6 |

[a] 7 days post innoculation  
[b] Control plants were 100% infected

TABLE 20

CONTROL OF DOWNY MILDEW IN CUCUMBER BY BABA, METALAXYL SINGLE ISOMER, MANCOZEB AND THEIR MIXTURES[a]

| Compounds | Ratio | 4 | 16 | 62 | 250 | 1000 | $ED_{90}$ mg/L | CF |
|---|---|---|---|---|---|---|---|---|
| BABA | — | 8 | 8 | 8 | 38 | — | 2155 | — |
| mancozeb |  | 0 | 8 | 23 | 72 | — | 315 | — |
| Metalaxyl Single Isomer |  | 0 | 0 | 0 | 8 | — | 844 | — |
| BABA + mancozeb + Metalaxyl Single Isomer | 55 + 40 + 5 | 23 | 23 | 54 | 75 | — | 313 | 2.0 |
|  | 50 + 40 + 10 | 38 | 25 | 31 | 80 | — | 314 | 2.0 |
|  | 40 + 40 + 20 | 8 | 15 | 8 | 31 | — | 689 | 0.9 |
|  | 45 + 50 + 5 | 8 | 8 | 54 | 72 | — | 309 | 1.7 |
|  | 40 + 50 + 10 | 8 | 31 | 54 | 89 | — | 228 | 2.3 |
|  | 30 + 50 + 10 | 8 | 15 | 31 | 83 | — | 273 | 1.9 |
|  | 35 + 60 + 5 | 54 | 54 | 78 | 86 | — | 239 | 2.0 |
|  | 30 + 60 + 10 | 46 | 38 | 54 | 85 | — | 268 | 1.7 |
|  | 20 + 60 + 20 | 61 | 69 | 69 | 83 | — | 281 | 1.6 |
|  | 25 + 70 + 5 | 38 | 46 | 78 | 97 | — | 139 | 3.0 |
|  | 20 + 70 + 10 | 38 | 23 | 63 | 94 | — | 194 | 2.1 |
|  | 10 + 70 + 20 | 38 | 69 | 23 | 78 | — | 362 | 1.1 |

[a] 6 days post innoculation  
[b] Control plants were 81% infected

TABLE 21

CONTROL OF DOWNY MILDEW IN CUCUMBER BY BABA, ALIETTE, CYMOXANIL AND THEIR MIXTURES

| Compounds | Ratio | Percent Disease Control[a] @ mg/L Active Ingredient | | | | $ED_{90}$ | CF |
|---|---|---|---|---|---|---|---|
| | | 16 | 62 | 250 | 1000 | mg/L | |
| BABA | | 37 | 67 | 76 | 85 | 975 | — |
| Aliette | | 45 | 85 | 98 | 99 | 245 | — |
| Cymoxanil | | 0 | 20 | 58 | 72 | 1229 | — |
| BABA + Aliette + Cymoxanil | | | | | | | |
| | 60 + 25 + 15 | 63 | 70 | 88 | 95 | 584 | 1.0 |
| | 25 + 60 + 15 | 70 | 85 | 98 | 100 | 100 | 3.4 |

[a]Control plants were 100% infected

TABLE 22

CONTROL OF DOWNEY MILDEW IN CUCUMBER BY BABA, MANCOZEB, CYMOXANIL AND THEIR MIXTURES

| Compounds | Ratio | Percent Disease Control[a] @ mg/L Active Ingredient | | | | | $ED_{90}$ | CF |
|---|---|---|---|---|---|---|---|---|
| | | 4 | 16 | 62 | 250 | 1000 | mg/L | |
| BABA | | — | 0 | 13 | 50 | 63 | 1413 | — |
| Mancozeb | | 75 | 87 | 90 | 92 | — | 167 | — |
| Cymoxanil | | 13 | 25 | 38 | 50 | — | 506 | — |
| BABA + Mancozeb + Cymoxanil | | | | | | | | |
| | 60 + 25 + 15 | 63 | 75 | 83 | 95 | | 152 | 3.0 |
| | 25 + 60 + 15 | 75 | 87 | 90 | 95 | | 136 | 1.8 |

[a]Control plants were 100% infected

TABLE 23

CONTROL OF DOWNY MILDEW IN CUCUMBER BY BABA, BAYER SZX (FENCARAMID) AND THEIR MIXTURES

| Compounds | Ratio | Percent Disease Control[b] @ mg/L Active Ingredient | | | | | | | $ED_{90}$ | CF |
|---|---|---|---|---|---|---|---|---|---|---|
| | | 2 | 8 | 31 | 125 | 500 | 1000 | 2000 | mg/L | |
| BABA | | | | | | 61 | 72 | 74 | 2354 | |
| FENCARAMID | | 78 | 83 | 95 | 100 | | | | 19 | |
| BABA + FENCARAMID | | | | | | | | | | |
| | 80 + 20 | 38 | 58 | 83 | 100 | | | | 33 | 2.8 |
| | 50 + 50 | 60 | 80 | 98 | 100 | | | | 14 | 2.7 |
| | 20 + 80 | 78 | 85 | 98 | 100 | | | | 13 | 1.8 |

[a]5 days innoculation
[b]Control plants were 81% infected

TABLE 24

CONTROL OF DOWNY MILDEW IN CUCUMBER BY BABA, BAYER DIMETHOMORPH (DMN) AND THEIR MIXTURES

| Compounds | Ratio | Percent Disease Control[b] @ mg/L Active Ingredient |
|---|---|---|
| BABA 1000 | gave | 17% Control |
| DMN 5 ppm | gave | 32% Control |

TABLE 24-continued

CONTROL OF DOWNY MILDEW IN CUCUMBER BY BABA, BAYER DIMETHOMORPH (DMN) AND THEIR MIXTURES

| Compounds | Ratio | Percent Disease Control[b] @ mg/L Active Ingredient |
|---|---|---|
| BABA + DMN 1000 + 5 ppm | gave | 74% Control |

$$\text{Synergy ratio} = \frac{74 = 74}{\frac{17 = 32 - (17\ 32)\ 33}{100}} = 2.24$$

TABLE 25

CONTROL OF DOWNY MILDEW IN CUCUMBER BY BABA, FOLPET, CYMOXANIL AND THEIR MIXTURES[a]

| Compounds | Ratio | Percent Disease Control[b] @ mg/L Active Ingredient | | | | $ED_{90}$ | CF |
|---|---|---|---|---|---|---|---|
| | | 16 | 62 | 250 | 1000 | mg/L | |
| BABA | | 6 | 22 | 48 | 82 | 1072 | |
| FOLPET | | 43 | 84 | 95 | 97 | 403 | |
| | | 48 | 63 | 82 | 97 | 524 | |
| BABA + FOLPET + CYMOXANIL | | | | | | | |
| | 25 + 60 + 15 | 76 | 87 | 95 | 99 | 247 | 2.0 |

[a]5 days post inoculation
[b]Control plants were 95% infected

TABLE 26

CONTROL OF DOWNY MILDEW IN CUCUMBER BY BABA, PHOSETYL-ALUMINIUM AND THELR MIXTURES[a]

| Compounds | Ratio | Percent Disease Control[b] mg/L Active Ingredient | | | | $ED_{90}$ mg/L | CF |
|---|---|---|---|---|---|---|---|
| | | 16 | 62 | 250 | 1000 | | |
| BABA | | 10 | 43 | 43 | 71 | 1386 | — |
| Phosetyl-Aluminium | | 71 | 71 | 94 | 86 | 638 | — |
| BABA + Phosetyl-Aluminium | | | | | | | |
| | 12 + 88 | 43 | 43 | 86 | 100 | 261 | 4.7 |
| | 25 + 75 | 0 | 14 | 71 | 97 | 551 | 1.9 |
| | 50 + 50 | 0 | 14 | 57 | 83 | 1009 | 0.9 |
| | 75 + 25 | — | 57 | 57 | 86 | 918 | 0.8 |
| | 88 + 12 | 14 | 29 | 71 | 86 | 931 | 0.7 |

[a]7 days post innoculation
[b]control plants were 88% infected

TABLE 27

CONTROL OF LATE BLIGHT IN POTATO BY BABA, BION AND THEIR MIXTURES[a]

| Compounds | Ratio (w/w) | Percent Disease Control mg/L Active Ingredient | | | $ED_{90}$ mg/L | CF |
|---|---|---|---|---|---|---|
| | | 250 | 500 | 1000 | | |
| BABA | 38 | 75 | 93 | 776 | — | |
| BION | 13 | 25 | 78 | 1173 | — | |
| BABA + ACIBENZOLAR-S-METHYL (10 + 1) | | 38 | 78 | 98 | 639 | 1.3 |

TABLE 28

CONTROL OF LATE BLIGHT IN TOBACCO BY BABA, AZOXYSTROBINE MIXTURE AND THEIR MIXTURES, FUNGAL ISOLATE = R

| Compounds | Ratio (w/w) | Percent Disease Control mg/L Active Ingredient | | | | | | $ED_{90}$ mg/L | CF |
|---|---|---|---|---|---|---|---|---|---|
| | | 5 | 10 | 25 | 50 | 100 | 200 | | |
| BABA | | — | — | — | 0 | 13 | 100 | 171 | |
| AZOXYSTROBINE | 13 | 81 | 81 | 81 | 93 | — | — | 27 | |
| BABA + AZOXYSTROBINE | | | | | | | | | |
| 5 + 1 | | | | 25 | 100 | 100 | 100 | 41 | 2.2 |
| 10 + 1 | | | | 38 | 81 | 100 | 100 | 54 | 2.1 |
| 15 + 1 | | | | 50 | 81 | 100 | 100 | 53 | 2.4 |

TABLE 29

CONTROL OF DOWNY MILDEW IN TOBACCO BY BABA, ACIBENZOLAR-S-METHYL, RIDOMTL-GOLD AND THELR MIXTURES: Fungal isolate = R

| Compounds | Ratio (w/w) | Percent Disease Control mg/L Active Ingredient | | | $ED_{90}$ mg/L | CF |
|---|---|---|---|---|---|---|
| | | 16 | 62 | 250 | | |
| BABA | — | 3 | 27 | 51 | 406 | |
| BION | — | 76 | 76 | 99 | 88 | |
| RIDOMILGOLD | — | 49 | 37 | 58 | 416 | |
| BABA + ACIBENZOLAR-S-METHYL | 75 + 1 | 48 | 78 | 99 | 90 | 3.1 |
| | 10 + 1 | 45 | 93 | 100 | 52 | 5.9 |
| | 15 + 1 | 22 | 84 | 91 | 186 | 1.8 |
| | 20 + 1 | 14 | 74 | 98 | 116 | 3.5 |

TABLE 29-continued

CONTROL OF DOWNY MILDEW IN TOBACCO BY BABA,
ACIBENZOLAR-S-METHYL, RIDOMTL-GOLD
AND THELR MIXTURES: Fungal isolate = R

| Compounds | Ratio (w/w) | Percent Disease Control mg/L Active Ingredient |  |  | ED$_{90}$ mg/L | CF |
|---|---|---|---|---|---|---|
|  |  | 16 | 62 | 250 |  |  |
| BABA + RIDOMIL GOLD | 7.5 + 1 | 27 | 63 | 97 | 150 | 2.7 |
|  | 10 + 1 | 34 | 44 | 99 | 145 | 2.8 |
|  | 15 + 1 | 23 | 52 | 78 | 282 | 1.4 |
|  | 20 + 1 | 0 | 20 | 91 | 239 | 1.4 |
| BABA + ACIBENZOLAR-S-METHYL + RIDOMIL-GOLD | 7.5 + 1 + 1 | 37 | 63 | 95 | 174 | 1.7 |
|  | 10 + 1 + 1 | 45 | 71 | 92 | 190 | 1.7 |
|  | 15 + 1 + 1 | 37 | 84 | 82 | 230 | 1.5 |
|  | 20 + 1 + 1 | 57 | 98 | 98 | 84 | 4.2 |

TABLE 30

CONTROL OF DOWNY MILDEW IN TOBACCO BY BABA,
ACIBENZOLAR-S-METHYL, CURZATE RIDOMIL-GOLD
AND THEIR MIXTURES: Fungal isolate = R

| Compounds | Ratio (w/w) | Percent Disease Control mg/L Active Ingredient |  |  | ED$_{90}$ mg/L | CF |
|---|---|---|---|---|---|---|
|  |  | 100 | 200 | 400 |  |  |
| BABA | — | 37 | 62 | 100 | 270 | — |
| ACIBENZOLAR-S-METHYL | — | 37 | 50 | 80 | 443 | — |
| CURZATE | — | 25 | 25 | 62 | 596 | — |
| RIDOMILGOLD | — | 20 | 35 | 42 | >1000 | — |
| BABA + ACIBENZOLAR-S-METHYL | 10 + 1 | 62 | 100 | 100 | 113 | 2.3 |
|  | 15 + 1 | 50 | 100 | 100 | 118 | 2.3 |
| BABA + CURZATE | 10 + 1 | 62 | 100 | 100 | 113 | 2.5 |
|  | 5 + 1 | 37 | 62 | 100 | 270 | 1.1 |

TABLE 31

CONTROL OF DOWNY MILDEW IN TOBACCO BY BABA,
ACIBENZOLAR-S-METHYL, RIDOMIL-GOLD
AND THEIR MIXTURES: Fungal isolate = S

| Compounds | Ratio (w/w) | Percent Disease Control mg/L Active Ingredient |  |  | ED$_{90}$ mg/L | CF |
|---|---|---|---|---|---|---|
|  |  | 0.5 | 5 | 50 |  |  |
| BABA | — | 0 | 27 | 59 | 78 | — |
| ACIBENZOLAR-S-METHYL | — | 54 | 76 | 85 | 52 | — |
| RIDOMILGOLD | — | 100 | 100 | 100 | 0.2 | — |
| BABA + ACIBENZOLAR-S-METHYL | 7.5 + 1 | 85 | 85 | 99 | 15 | 4.9 |
|  | 10 + 1 | 86 | 94 | 100 | 4 | 18.7 |
|  | 15 + 1 | 75 | 84 | 100 | 5 | 15.1 |
| BABA + RIDOMIL-GOLD | 7.5 + 1 | 94 | 100 | 100 | 0.5 | 3.3 |
|  | 10 + 1 | 99 | 100 | 100 | 0.4 | 5.4 |
|  | 15 + 1 | 88 | 90 | 100 | 4.3 | 2.1 |
| BABA + ACIBENZOLAR-S-METHYL + RIDOMIL-GOLD | 7.5 + 1 + 1 | 99 | 100 | 100 | 0.4 | 4.4 |
|  | 10 + 1 + 1 | 100 | 100 | 100 | 0.2 | 12.2 |
|  | 15 + 1 + 1 | 73 | 100 | 100 | 0.6 | 5.3 |

TABLE 32

CONTROL OF DOWNY MILDEW IN GRAPES BY BABA, ACIBENZOLAR-S-METHYL AND THEIR MIXTURES IN LEAF DISCS

| Compounds | Ratio (w/w) | Percent Disease Control mg/L Active Ingredient | | | | | | $ED_{90}$ mg/L | CF |
|---|---|---|---|---|---|---|---|---|---|
| | | 0.31 | 1.25 | 5 | 20 | 50 | 100 | | |
| BABA | — | — | — | 15 | 93 | 95 | 99 | 38 | — |
| ACIBENZOLAR-S-METHYL | 0 | 27 | 75 | 100 | — | — | 6 | — | |
| BABA + ACIBENZOLAR-S-METHYL | 10 + 1 | 0 | 37 | 68 | 100 | — | — | 6.6 | 3.9 |
| | 15 + 1 | 60 | 82 | 100 | 100 | — | — | 1.4 | 19.8 |

TABLE 33

CONTROL OF DOWNY MILDEW IN GRAPES BY BABA, ALLIETTE AND THEIR MIXTURES IN LEAF DISCS

| Compounds | Ratio (w/w) | Percent Disease Control mg/L Active Ingredient | | | | | | $ED_{90}$ mg/L | CF |
|---|---|---|---|---|---|---|---|---|---|
| | | 1.25 | 2.5 | 5 | 10 | 20 | 50 | | |
| BABA | — | — | 38 | 44 | 81 | 86 | 92 | 33 | — |
| ALLIETTE | 13 | 36 | 38 | 40 | 48 | 81 | — | 24 | |
| BABA + ALLIETTE | 1 + 1 | 44 | 81 | 87 | 89 | 92 | — | 12 | 2.3 |
| | 3 + 1 | 44 | 69 | 88 | 92 | 95 | — | 10 | 3.0 |
| | 5 + 1 | 25 | 31 | 43 | 47 | 83 | — | 22 | 1.4 |
| | 7 + 1 | 24 | 31 | 34 | 56 | 62 | — | 30 | 1.0 |
| | 9 + 1 | 22 | 34 | 39 | 55 | 61 | — | 31 | 1.0 |

TABLE 34

CONTROL OF DOWNY MILDEW IN GRAPES BY BABA, CURZATE AND THEIR MIXTURES, IN LEAF DISCS

| Compounds | Ratio (w/w) | Percent Disease Control mg/L Active Ingredient | | | | | | $ED_{90}$ mg/L | CF |
|---|---|---|---|---|---|---|---|---|---|
| | | 1.25 | 2.5 | 5 | 10 | 20 | 50 | | |
| BABA | — | — | 25 | 36 | 78 | 83 | 91 | 36 | — |
| CURZATE | | 11 | 39 | 58 | 66 | 55 | — | 27 | — |
| BABA + CURZATE | 1 + 1 | 51 | 61 | 68 | 81 | 89 | — | 16 | 1.9 |
| | 3 + 1 | 62 | 70 | 77 | 86 | 93 | — | 13 | 2.6 |
| | 5 + 1 | 69 | 74 | 81 | 89 | 95 | — | 11 | 3.1 |
| | 7 + 1 | 49 | 68 | 74 | 78 | 89 | — | 16 | 2.2 |
| | 9 + 1 | 21 | 39 | 58 | 73 | 82 | — | 17 | 2.1 |

TABLE 35

CONTROL OF DOWNY MILDEW IN GRAPES BY BABA, DIMETHOMORPH AND THEIR MIXTURES, IN LEAF DISCS

| Compounds | Ratio (w/w) | Percent Disease Control mg/L Active Ingredient | | | | | $ED_{90}$ mg/L | CF |
|---|---|---|---|---|---|---|---|---|
| | | 0.31 | 1.25 | 5 | 20 | 50 | | |
| BABA | — | — | — | 0 | 10 | 60 | 90 | 44 | — |
| DIMETHOMORPH | | 40 | 30 | 60 | 90 | — | 19 | — | |
| BABA + DIMETHOMORPH | 1 + 1 | 10 | 30 | 80 | 100 | | 6 | 4.4 |
| | 3 + 1 | 30 | 60 | 60 | 60 | | 28 | 1.2 |
| | 5 + 1 | 0 | 0 | 20 | 60 | | 30 | 1.2 |
| | 7 + 1 | 0 | 0 | 10 | 50 | | 34 | 1.1 |
| | 9 + 1 | 0 | 40 | 50 | 40 | | 40 | 1.0 |

What is claimed is:

1. Synergistic fungicidal composition comprising synergistically effective respective amounts of D,L-3-aminobutyric acid and Mancozeb.

2. A composition in accordance with claim 1 wherein the D,L-3-aminobutyric acid and Mancozeb are present in a weight ratio of 9:1 to 1:9.

3. The composition of claim 2 wherein said weight ratio is 4:1 to 1:4.

4. A method of administering a fungicidal composition in accordance with claim 1 to a plant infested with fungus, wherein the fungus is selected from the group consisting of *Phytophthora infestans, Pseudoperonspora Cubensis, Plasmopara veticola,* and *Peronospora tabacina*.

5. A method in accordance with claim 4 wherein the fungus is selected from the group consisting of *Phytophthora infestans* in potatoes and tomatoes, *Pseudoperonspora Cubensis* in cucumber and melons, *Plasmopara veticola* in grapes, and *Peronospora tabacina* in tobacco.

6. A method of controlling fungal infections in plants comprising applying to the plants or parts thereof a synergistic fungicidal composition comprising synergistically effective respective amounts of D,L-3-aminobutyric acid and Mancozeb.

7. A method in accordance with claim 6 which comprises applying D,L-3-aminobutyric acid and Mancozeb in a weight ratio of 9:1 to 1:9.

8. A method in accordance with claim 6 wherein the plants are selected from the group consisting of potatoes, tomatoes, cucumbers, melons, grape vines, and tobacco.

9. A method in accordance with claim 6 wherein the fungus is selected from the group consisting of *Phytophthora infestans, Pseudoperonspora Cubensis, Plasmopara veticola,* and *Peronospora tabacina*.

10. A method in accordance with claim 9 wherein the fungus is selected form the group consisting of *Phytophthora infestans* in potatoes and tomatoes, *Pseudoperonspora Cubensis* in cucumber and melons, *Plasmopara veticola* in grapes, and *Peronospora tabacina* in tobacco.

11. The method of claim 7 wherein said ratio is 4:1 to 1:4.

* * * * *